United States Patent
Brunner

Patent Number: 6,025,519
Date of Patent: Feb. 15, 2000

[54] PROCESS FOR PREPARING CYCLOBUTANE-1,2-DICARBOXYLIC ESTERS

[75] Inventor: Andreas Brunner, Brig, Switzerland

[73] Assignee: Lonza, Ltd., Gampel/Valais, Switzerland

[21] Appl. No.: 09/118,882

[22] Filed: Jul. 20, 1998

[30] Foreign Application Priority Data

Jul. 22, 1997 [CH] Switzerland .............................. 1772/97

[51] Int. Cl.[7] .......................... C07C 69/74; C07D 319/06
[52] U.S. Cl. .......................... 560/123; 549/333; 549/342; 549/420; 549/475
[58] Field of Search ............................ 560/123; 549/333, 549/342, 475, 332, 420

[56] References Cited

U.S. PATENT DOCUMENTS

| | | | |
|---|---|---|---|
| 5,233,076 | 8/1993 | Ahmad | 560/106 |
| 5,344,962 | 9/1994 | Ahmad | 560/123 |

*Primary Examiner*—John Kight
*Assistant Examiner*—Charanjit S. Aulakh
*Attorney, Agent, or Firm*—Fisher, Christen&Sabol

[57] ABSTRACT

Cyclobutane-1,2-dicarboxylic esters of the formula:

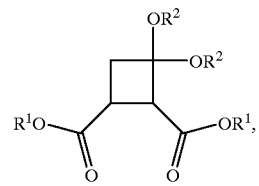

I in which $R^1$ is a $C_{1-8}$-alkyl group, an optionally substituted mono- or bicyclic cycloaliphatic group having 3 to 10 ring carbon atoms, an optionally substituted aryl or arylalkyl group or an optionally substituted saturated heterocyclic group and $R^2$ is either $C_{1-4}$-alkyl or both radicals $R^2$ together form a group of the formula $-(CH_2)_n-$ (n is 2 to 4), are prepared from the corresponding maleic or fumaric esters and ketene acetals in the presence of a Lewis acid and a sterically hindered base. The reaction is stereoselective when optically active maleic or fumaric esters are employed. The cyclobutane-1,2-dicarboxylic esters (I), in particular those having trans configuration, are intermediates in the synthesis of pharmaceutically active compounds.

17 Claims, No Drawings

PROCESS FOR PREPARING CYCLOBUTANE-1,2-DICARBOXYLIC ESTERS

This application claims priority benefit of foreign application No. 1772/97, filed Jul. 22, 1997.

BACKGROUND OF THE INVENTION

1. Field of the Invention

The present invention relates to a process for preparing cyclobutane-1,2-dicarboxylic esters (I) by [2+2]-cycloaddition of ketene acetals and fumaric or maleic esters.

The compounds preparable according to the invention are of the general formula:

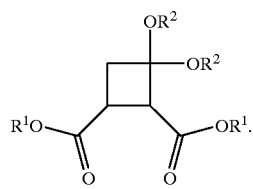

I

In this formula, $R^1$ is a $C_{1-8}$-alkyl group, an optionally substituted mono- or bicyclic cycloaliphatic group having 3 to 10 ring carbon atoms, an optionally substituted aryl or arylalkyl group or an optionally substituted saturated heterocyclic group and $R^2$ is $C_{1-4}$-alkyl or both radicals $R^2$ together are $-(CH_2)_n-$ where n is 2 to 4.

Here and below, $C_{1-4}$- or $C_{1-8}$-alkyl groups are in each case all straight-chain or branched primary, secondary or tertiary alkyl groups having 1 to 4 and 1 to 8 carbon and tert-butyl and $C_{1-8}$-alkyl additionally includes, for example, pentyl, isopentyl, neopentyl, hexyl or octyl. Mono- or bicyclic cycloaliphatic groups having 3 to 10 carbon atoms are, for example, groups such as cyclopropyl, cyclobutyl, cyclopentyl, cyclohexyl, cycloheptyl, norbornan-x-yl, norcaran-x-yl or norpinan-x-yl, where the "x" represents any position of attachment desired. These groups can also carry one or more substituents, for example, $C_{1-4}$-alkyl groups. These substituted cycloaliphatic groups include, for example, menthan-x-yl, bornan-x-yl, caran-x-yl, pinan-x-yl or thujan-x-yl. Aryl groups are aromatic hydrocarbon radicals having one or more rings, i.e., for example, phenyl, x-naphthyl, anthracen-x-yl, phenanthren-x-yl, fluoren-x-yl or biphenyl-x-yl. The rings in radicals having a plurality of rings can also be partially hydrogenated, such as, tetrahydronaphthalen-x-yl, indan-x-yl or acenaphthen-x-yl. Examples of arylalkyl groups include benzyl, 1-phenylethyl, 2-phenylethyl (phenethyl) or diphenylmethyl (benzhydryl). Saturated heterocyclic groups include, for example, tetrahydrofuryl or tetrahydropyranyl. These aryl, arylalkyl or saturated heterocyclic groups can optionally carry one or more identical or different substituents, such as, $C_{1-4}$-alkyl groups or halogen atoms, for example.

The compounds which are preparable according to the invention, in particular those having trans configuration at the cyclobutane ring, are intermediates in the synthesis of pharmaceutically active compounds, for example, of antiviral nucleoside analogues (European Published Patent Application No. 0458643).

2. Background Art

It is known that 3,3-dialkoxycyclobutane-1,2-dicarboxylic esters can be prepared from fumaric or maleic esters and ketene acetals by [2+2]-cycloaddition. Since the cycloaddition proceeds in a stereospecific manner, fumaric esters give products having trans configuration at the cyclobutane ring, usually in the form of a racemate. Furthermore, it is known that if esters of fumaric acid in combination with optically active alcohols are employed, mixtures of diastereomers are obtained in which one of the two stereoisomers [depending on the nature and the configuration of the alcohol component either that having (1S) or that having (1R) configuration at the cyclobutane ring] prevails [European Published Patent Application No. 0458643, Example 1; S. Ahmad, Tetrahedron Lett., (1991), 32, 6997–7000]. The process requires the use of at least two equivalents of dialkylaluminium chloride. A further disadvantage of this process consists in the fact that it has to be carried out at low temperatures of, for example, −75° C. to obtain good yields. On an industrial scale, however, such low temperatures can only be achieved at considerable cost.

BROAD DESCRIPTION OF THE INVENTION

Accordingly, it is an object of the present invention to provide a process which does not require a large excess of expensive dialkylaluminium chloride and which can be carried out at temperatures which are less low. According to the invention, this object is achieved by the process of the invention.

Surprisingly, it has been found that when dicarboxylic esters of the general formula:

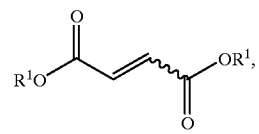

II in which $R^1$ is as defined above, are reacted with a ketene acetal of the general formula:

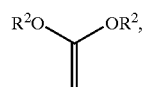

III in the presence of a Lewis acid by addition of a sterically hindered base to the reaction mixture, it is possible not only to obtain an improved yield, but it is also possible to carry out the reaction with a reduced excess of Lewis acid (for example, dialkylaluminium chloride) and at a higher temperature (up to approximately +20° C. and above).

In a preferred embodiment of the process according to the invention, the dicarboxylic ester (II) employed is a fumaric ester of the general formula:

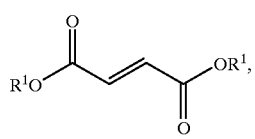

IIa in which $R^1$ is as defined above, and a cyclobutane-trans-1,2-dicarboxylic ester of the general formula:

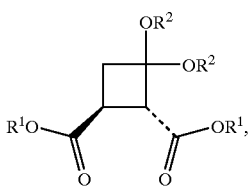

Ia and/or the mirror image, in which $R^1$ and $R^2$ are as defined above, is obtained.

In another embodiment, the dicarboxylic ester (II) employed is a maleic ester of the general formula:

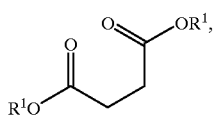

IIb in which $R_1$ is as defined above, and a cyclobutane-cis-1,2-dicarboxylic ester of the general formula:

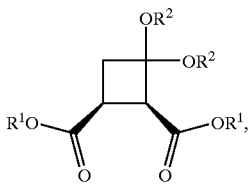

Ib and/or the mirror image, in which $R^1$ and $R^2$ are as defined above, is obtained.

Preference is given to using those dicarboxylic esters (II) in which $R^1$ contains at least one chiral element, namely, in non-racemic form. Particularly preferably, these non-racemic dicarboxylic esters (II) are essentially optically pure. The cyclobutane-1,2-dicarboxylic ester stereoisomers (I) obtained from chiral dicarboxylic esters (II) are not enantiomers, but diastereomers which differ in their physical properties and which can be separated more or less easily. With these dicarboxylic esters (II), the [2+2]-cycloaddition proceeds stereoselectively with respect to the absolute configuration of the resulting cyclobutane ring, so that one diastereomer is preferably formed.

Chiral radical $R^1$ which are preferably used are radicals such as 1-phenylethyl, menthyl and its stereoisomers, bornyl and its stereoisomers, dihydro-4,4-dimethyl-furan-2-(3H)-on-3-yl (derived from pantolactone), 1-(methoxycarbonyl)ethyl or 1-(ethoxycarbonyl)ethyl (derived from methyl lactate or ethyl lactate). Particular preference is given to menthyl. Using optically pure dimenthyl fumarates, very good diastereoselectivities can be achieved, and it is possible to obtain cyclobutane-trans-1,2-dicarboxylic esters (Ia) having de values [de=diastereomeric excess, defined as quotient $|A-B|:(A+B)$, where A and B represent the amounts of the two diastereomers] of up to 90 percent and more, which are virtually stereoisomerically pure after a simple purification step (for example recrystallization).

In particular, (1R)-menthyl fumarates [IIa, $R^1$=(1R)-menthyl] yield predominantly cyclobutane-trans-1,2-dicarboxylic esters (Ia) in the (1S) configuration of the cyclobutane ring.

Ketene acetals (III) which are preferably used are those in which $R^2$ is methyl or ethyl or both radicals $R^2$ together are —$(CH_2)_4$—. Specifically, these are ketene dimethyl acetal, ketene diethyl acetal and 2-methylene-1,3-dioxepane.

Suitable Lewis acids are, for example, organoaluminium and organotitanium compounds of the general formulae $R_2AlCl$, $RAlCl_2$, $Al(OR)_3$, $Ti(OR)_2Cl_2$, $Ti(OR)_4$ in which the radicals R are identical or different and each represent a $C_{1-8}$-alkyl group, and also halides such as $AlCl_3$, $TiCl_4$, $BF_3$, $ZnCl_2$, $ZnBr_2$, $ZrCl_4$ and $SnCl_4$. The Lewis acid which is preferably used is a dialkylaluminium chloride of the general formula $R_2AlCl$. Particular preference is given to those dialkylaluminium chlorides in which R is ethyl or isobutyl.

Suitable sterically hindered bases are in particular tertiary amines, such as, 2,6-di-tert-butylpyridine, 2,6-di-tert-butylpyridine bound to a polymeric support, 2,6-di-tert-butyl-4-methylpyridine, triethylamine, diethylisopropylamine, triisopropylamine and N-ethyldicyclohexylamine. Particular preference is given to ethyldiisopropylamine ("Hünigs base").

DETAILED DESCRIPTION OF THE INVENTION

The examples below illustrate the practice of the process according to the invention without limiting it.

EXAMPLE 1

Di-(1R)-menthyl (1S,2R)-3,3-diethoxy-1,2-cyclobutanedicarboxylate

At room temperature and under argon, 30.0 g (76.5 mmol) of di-(1R)-menthyl fumarate was dissolved in 250 ml of toluene in a double-jacket flask cooled by a circulation cryostat. The solution was cooled to −21° C. and admixed with 16.5 ml (84.5 mmol) of diisobutylaluminium chloride over a period of 15 min. After a further 5 min., 5.2 ml (30.4 mmol) of ethyldiisopropylamine was added. The mixture was stirred for another 5 min. and then, with enhanced cooling (coolant temperature: −24° C.), admixed with 11.1 ml (84.1 mmol) of ketene diethyl acetal over a period of 15 min., the internal temperature rising to −19° C. The dark reaction mixture was stirred for another 40 min. at −22° to −20° C. and then poured onto a mixture of 200 ml of n-hexane, 200 ml of saturated aqueous sodium bicarbonate solution and a little ice. The resultant orange emulsion was stirred until it had reached room temperature. The phases were subsequently separated and the aqueous phase was extracted with 2×200 ml of hexane. The combined organic phases were washed two times each with saturated sodium bicarbonate solution and saturated sodium chloride solution, filtered through Celite® and dried over sodium sulfate. The solvent was distilled off under reduced pressure and the residue was dried under high vacuum. The crude product obtained in this manner (40.38 g, orange solid) contained, according to NMR, no unreacted starting material and consisted, according to GC, of a mixture of the (1S,2R)- and (1R,2S)-diastereomers in a ratio of 93.5:6.5 (87 percent de). For purification, 39.1 g of the crude product was dissolved in 1.2 l of methanol/water (95:5), cooled to room temperature with stirring and left to stand at 0° C. overnight. The yellowish crystals which had precipitated were filtered off, washed with a little methanol/water and dried under high vacuum. The yield was 27.9 g (74 percent, based on dimenthyl fumarate), diastereomerically pure.

EXAMPLE 2

Di-(1R)-menthyl (1S,2R)-3,3-dimethoxy-1,2-cyclobutanedicarboxylate

By the method of Example 1, di-(1R)-menthyl fumarate was reacted at −40° C. with ketene dimethyl acetal in the presence of 0.2 equivalents of ethyldiisopropylamine and 2 equivalents of diethylaluminium chloride. $^1$H NMR analysis of the reaction mixture showed that the yield was quantitative and the de value was >80 percent.

Comparative Example 1

Di-(1R)-menthyl (1S,2R)-3,3-dimethoxy-1,2-cyclobutanedicarboxylate

Example 2 was repeated, but without addition of ethyldiisopropylamine. $^1$H NMR analysis of the reaction mixture showed that the yield was 37 percent and the de value was >80 percent.

EXAMPLE 3

Di-(1R)-menthyl (1S,2R)-5,10-dioxaspiro [3.6] decane-1,2-dicarboxylate

[I, $R^1$=(1R)-menthyl, $2R^2$=—$(CH_2)_4$—]

By the method of Example 1, di-(1R)-menthyl fumarate was reacted at −20° C. with 2-methylene-1,3-dioxepane (ketene tetramethylene acetal) in the presence of 0.2 equivalents of ethylidisopropylamine and 2 equivalents of diethylaluminium chloride. $^1$H NMR analysis of the reaction mixture showed that the yield was 93 percent, and only one diastereomer could be detected. A repetition of the experiment at a reaction temperature of 0° C. gave the same result.

Comparative Example 2

Di-(1R)-menthyl (1S,2R)-5,10-dioxaspiro [3.6] decane-1,2-dicarboxylate

Example 3 was repeated, but without addition of ethyldiisopropylamine. At a reaction temperature of −40° C., a yield of 73 percent was obtained, at 0° C. only 33 percent.

EXAMPLE 4

Diethyl (±)-3,3-diethoxy-trans-1,2-cyclobutanedicarboxylate

By the method of Example 1, diethyl fumarate was reacted at −40° C. with 2 equivalents of ketene diethyl acetal in the presence of 0.2 equivalents of ethyldiisopropylamine and 2 equivalents of diisobutylaluminium chloride. $^1$H NMR analysis of the reaction mixture showed that the yield was quantitative.

EXAMPLES 5 TO 14 and COMPARATIVE EXAMPLES 3 AND 4

Di-(1R)-menthyl (1S,2R)-3,3-diethoxy-1,2-cyclobutane-dicarboxylate

Example 1 was repeated, but the amounts of ketene diethyl acetal, ethyldiisopropylamine and dialkylaluminium chloride, and also the reaction temperature, the solvent and the alkyl radical in the dialkylaluminium chloride were varied. The conditions and the yields and de values determined by GC are summarized in Table 1 below.

TABLE 1

| Ex. No. | Acetal [Eq.] | Amine [Eq.] | Temp. [° C.] | R | $R_2AlCl$ [Eq.] | Solvent | Yield [%] | de [%] |
|---|---|---|---|---|---|---|---|---|
| 5 | 1.1 | 0.4 | −20° | Et | 2.0 | toluene | ≈100 | 86.6 |
| 6 | 1.1 | 0.4 | −20° | Bu | 2.0 | toluene | ≈100 | 90.7 |
| 7 | 1.1 | 0.4 | 0° | Et | 2.0 | toluene | 95 | 78.9 |
| 8 | 1.1 | 0.4 | 0° | Bu | 2.0 | toluene | ≈100 | 84.7 |
| 9 | 1.1 | 0.4 | +20° | Bu | 2.0 | toluene | ≈100 | 73 |
| 10 | 1.1 | 0.4 | −20° | Bu | 1.1 | toluene | ≈100 | 90.9 |
| 11 | 1.1 | 0.4 | −40° | Bu | 1.1 | toluene | ≈100 | 94.8 |
| 12 | 1.1 | 0.4 | −20° | Et | 2.0 | $CH_2Cl_2$ | ≈100 | 83.2 |
| 13 | 1.1 | 0.4 | −20° | Bu | 2.0 | $CH_2Cl_2$ | ≈100 | 83.1 |
| 14 | 1.1 | 0.4 | −20° | Bu | 1.1 | $C_2H_4Cl_2$ | ≈100 | 90.9 |
| C3 | 1.5 | — | −78° | Et | 2.0 | toluene | <10 | n.d. |
| C4 | 1.5 | — | −40° | Et | 2.0 | toluene | 29 | n.d. |

What is claimed is:

1. Process for preparing cyclobutane-1,2-dicarboxylic esters of the formula:

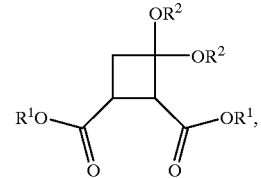

I in which $R^1$ is a $C_{1-8}$-alkyl groups, an optionally substitued mono- or bicyclic cycloaliphatic group having 3 to 10 ring carbon atoms, an optionally substituted aryl or arylalkyl group or an optionally substituted tetrahydrofuryl or tetrahydropyranyl group and $R^2$ is either $C_{1-4}$-alkyl or both radicals $R^2$ together form a group of the general formula —$(CH_2)_n$— where n is an integer from 2 to 4, comprising reacting a dicarboxylic ester of the formula:

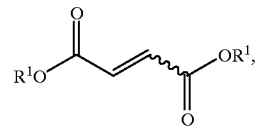

II in which $R^1$ is as defined above, with a ketene acetal of the formula:

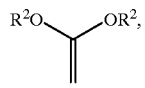

III in which $R^2$ is as defined above, in the presence of a Lewis acid, and a sterically hindered base.

2. The process according to claim 1, wherein the dicarboxylic ester (II) employed is a fumaric ester of the formula:

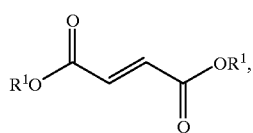

in which R¹ is as defined above, and a cyclobutane-trans-1,2-dicarboxylic ester of the formula:

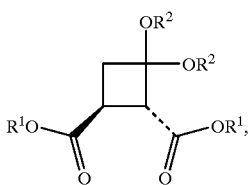

and/or the mirror image, in which R¹ and R² are as defined above, is obtained.

3. The process according to claim 1, wherein the dicarboxylic ester (II) employed is a maleic ester of the formula:

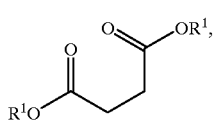

in which R¹ is as defined above, and a cyclobutane-cis-1,2-dicarboxylic ester of the formula:

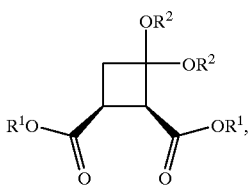

and/or the mirror image, in which R¹ and R² are as defined above, is obtained.

4. The process according to claim 3, wherein R¹ contains at least one chiral element and the dicarboxylic ester (II) is present in non-racemic form.

5. The process according to claim 4, wherein R¹ is selected from the group consisting of 1-phenylethyl, menthyl and bornyl and their stereoisomers, dihydro-4,4-dimethylfuran-2(3H)-on-3-yl, 1-(methoxycarbonyl)ethyl and 1-(ethoxycarbonyl)ethyl.

6. The process according to claim 5, wherein R¹ is (1R)-menthyl and the cyclobutane-trans-1,2-dicarboxylic ester (Ia) is obtained predominantly in the (1S) configuration.

7. The process according to claim 6, wherein R² is methyl or ethyl or both radicals R² together are —(CH$_2$)$_4$—.

8. The process according claim 7, wherein the Lewis acid employed is a dialkylaluminium chloride of the formula R$_2$AlCl, in which R is a C$_{1-8}$-alkyl group.

9. The process according to claim 8, wherein R is ethyl or isobutyl.

10. The process according to claim 9, wherein the sterically hindered base employed is ethyldiisopropylamine.

11. The process according to claim 1, wherein R¹ contains at least one chiral element and the dicarboxylic ester (II) is present in non-racemic form.

12. The process according to claim 11, wherein R¹ is selected from the group consisting of 1-phenylethyl, menthyl and bornyl and their stereoisomers, dihydro-4,4-dimethylfuran-2(3H)-on-3-yl, 1-(methoxycarbonyl)ethyl and 1-(ethoxycarbonyl)ethyl.

13. The process according to claim 2, wherein R¹ is (1R)-menthyl and the cyclobutane-trans-1,2-dicarboxylic ester (Ia) is obtained predominantly in the (1 S) configuration.

14. The process according to claim 1, wherein R² is methyl or ethyl or both radicals R² together are —(CH$_2$)$_4$—.

15. The process according to claim 1, wherein the Lewis acid employed is a dialkylaluminium chloride of the formula R$_2$AlCl, in which R is a C$_{1-8}$-alkyl group.

16. The process according to claim 15, wherein R is ethyl or isobutyl.

17. The process according to claim 1, wherein the sterically hindered base employed is ethyldiisopropylamine.

* * * * *